United States Patent
Zerhusen et al.

(10) Patent No.: US 11,523,956 B2
(45) Date of Patent: Dec. 13, 2022

(54) PATIENT SUPPORT APPARATUS TRANSPORT HANDLE

(71) Applicant: Hill-Rom Services, Inc., Batesville, IN (US)

(72) Inventors: Robert Mark Zerhusen, Cincinnati, OH (US); Jie Zhou, Batesville, IN (US); Neal Wiggermann, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 21 days.

(21) Appl. No.: 16/888,204

(22) Filed: May 29, 2020

(65) Prior Publication Data

US 2020/0375829 A1 Dec. 3, 2020

Related U.S. Application Data

(60) Provisional application No. 62/854,044, filed on May 29, 2019.

(51) Int. Cl.
*A61G 7/08* (2006.01)
*A61G 7/05* (2006.01)

(52) U.S. Cl.
CPC .............. *A61G 7/08* (2013.01); *A61G 7/05* (2013.01); *A61G 2200/32* (2013.01); *A61G 2203/32* (2013.01); *A61G 2203/38* (2013.01)

(58) Field of Classification Search
CPC .. B62B 5/0026; B62D 51/04; A61G 2203/32; A61G 2203/38; A61G 7/08; A61G 7/05; A61G 2200/32
USPC ........................................................ 702/41
See application file for complete search history.

(56) References Cited

U.S. PATENT DOCUMENTS

| 4,253,207 A | * 3/1981 | Marcyan ............. A61G 7/0533 |
| | | 5/84.1 |
| 7,419,019 B1 | 9/2008 | White et al. |
| 7,789,187 B2 | 9/2010 | Zerhusen et al. |
| 7,827,634 B2 | 11/2010 | Stroth et al. |
| 8,113,306 B2 | 2/2012 | Mass et al. |
| 9,027,183 B2 | 5/2015 | Childs et al. |
| 9,205,009 B2 | 12/2015 | Koors et al. |

(Continued)

FOREIGN PATENT DOCUMENTS

| JP | 2006000326 A | 1/2006 |
| WO | 2017194038 A1 | 11/2017 |

OTHER PUBLICATIONS

Jie Zhou, Neal Wiggermann, Ergonomic evaluation of brake pedal and push handle locations on hospital beds, Applied Ergonomics, 2017, 305-312, Elsevier.

*Primary Examiner* — David R Hare
*Assistant Examiner* — Adam C Ortiz
(74) *Attorney, Agent, or Firm* — Price Heneveld LLP (57) ABSTRACT

A patient support apparatus includes a frame. A vertical transport structure may be coupled with the frame. A grip is coupled with the vertical transport structure and at least one grip sensor is coupled to the grip on the vertical transport structure. A controller determines a vertical position of a user applied force applied to the at least one grip sensor and the controller activates a power drive mode upon determining that the push force has reached a threshold value corresponding to the vertical position of the user applied force and propel patient support apparatus.

15 Claims, 10 Drawing Sheets

(56) References Cited

U.S. PATENT DOCUMENTS

| | | |
|---|---|---|
| 9,463,126 B2 | 10/2016 | Zerhusen et al. |
| 9,707,143 B2 | 7/2017 | Thodupunuri et al. |
| 2010/0104410 A1* | 4/2010 | Groth .................. B62B 1/14 |
| | | 414/598 |
| 2016/0374874 A1* | 12/2016 | Trepanier ................ A61G 1/04 |
| | | 5/611 |
| 2019/0298590 A1* | 10/2019 | Patmore ............... A61G 1/0268 |

\* cited by examiner

PATENT SUPPORT APPARATUS TRANSPORT HANDLE

CROSS-REFERENCE TO RELATED APPLICATION

This application claims priority to and the benefit under 35 U.S.C. § 119(e) of U.S. Provisional Application No. 62/854,044, filed on May 29, 2019, entitled "PATIENT SUPPORT APPARATUS TRANSPORT HANDLE," the disclosure of which is hereby incorporated herein by reference in its entirety.

FIELD OF THE DISCLOSURE

The present disclosure generally relates to a patient support apparatus transport system, and more specifically to a height accommodating transport system with power drive capabilities.

SUMMARY OF THE DISCLOSURE

According to one aspect of the present disclosure, a patient support apparatus includes a frame. At least one wheel is coupled to the frame. A vertical transport handle is coupled with the frame and a grip is coupled with the vertical transport handle. At least one grip sensor is coupled to the grip at a vertical position on the vertical transport handle. A controller is configured to determine the vertical position of a user applied force to the grip sensor, determine an amount of user applied torque applied to the at least one grip sensor, determine a push force using the determined vertical position and the determined torque and in response to the push force reaching a threshold value, the controller responds by activating a power drive mode that rotates the at least one wheel to propel the patient support apparatus.

According to another aspect of the present disclosure, a patient support apparatus includes a frame. A vertical transport structure is coupled with the frame. A grip is coupled with the vertical transport structure and at least one grip sensor is coupled to the grip on the vertical transport structure. A controller determines a vertical position of a user applied force applied to the at least one grip sensor and the controller activates a power drive mode upon determining that the push force has reached a threshold value corresponding to the vertical position of the user applied force and propel patient support apparatus.

According to yet another aspect of the present disclosure, a patient support apparatus includes a frame. A vertical transport handle is coupled with the frame. The vertical transport handle includes an outer shaft. A grip is coupled with the outer shaft. An inner shaft is slidable within the outer shaft and includes a hook at an upper end thereof configured to secure an object. At least one grip sensor is provided in the grip. A controller is configured to determine a vertical position of a user applied force to the grip sensor, determine an amount of user applied force applied to the at least one grip sensor and in response to the user applied force reaching a threshold value the controller responds by activating a power drive mode wherein at least one wheel is rotated and the patient support apparatus is propelled.

These and other features, advantages, and objects of the present invention will be further understood and appreciated by those skilled in the art by reference to the following specification, claims, and appended drawings.

DETAILED DESCRIPTION

The present illustrated embodiments reside primarily in combinations of method steps and apparatus components related to a patient support apparatus transport handle system. Accordingly, the apparatus components and method steps have been represented, where appropriate, by conventional symbols in the drawings, showing only those specific details that are pertinent to understanding the embodiments of the present disclosure so as not to obscure the disclosure with details that will be readily apparent to those of ordinary skill in the art having the benefit of the description herein. Further, like numerals in the description and drawings represent like elements.

Figure 1:
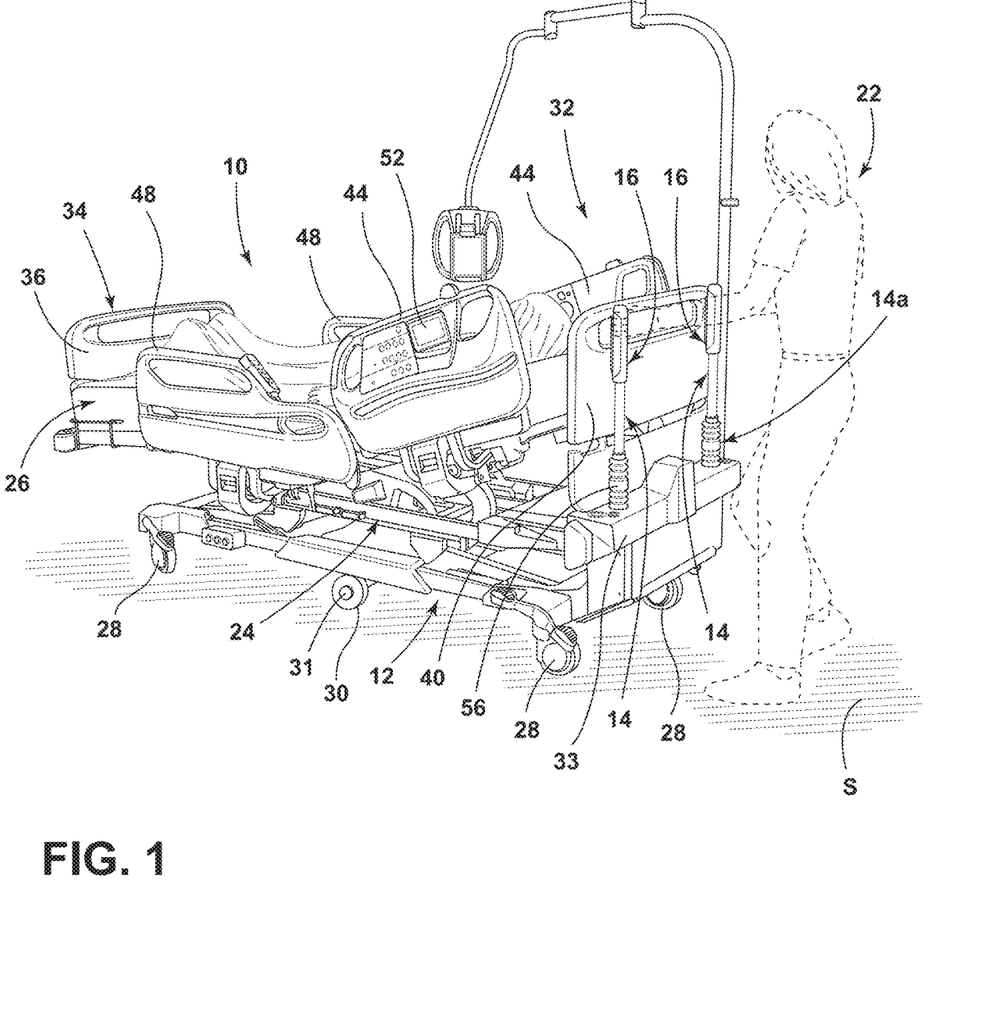
FIG. 1 is a is a top perspective view of a patient support apparatus, according to various aspects described herein.

For purposes of description herein, the terms "upper," "lower," "right," "left," "rear," "front," "vertical," "horizontal," and derivatives thereof shall relate to the disclosure as oriented in FIG. 1. Unless stated otherwise, the term "front" shall refer to a surface of the device closest to an intended viewer, and the term "rear" shall refer to a surface of the device furthest from the intended viewer. However, it is to be understood that the disclosure may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The terms "including," "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises a . . . " does not, without more constraints, preclude the existence of additional identical elements in the process, method, article, or apparatus that comprises the element.

Referring to FIGS. 1-3C reference numeral 10 generally designates a patient support apparatus in the form of a bed including a frame 12. At least one wheel 30 is coupled to the frame 12. A vertical transport handle 14 is coupled with the frame 12. The vertical transport handle 14 includes a grip 16 having at least one grip sensor 18 coupled to the grip 16 at a vertical position on the vertical transport handle 14. A controller 20 is configured to determine the vertical position of a user applied force to the grip sensor 18, determine an amount of user applied torque applied to the at least one grip sensor 18, determine a push force using the determined vertical position and the determined torque and in response to the push force reaching a threshold value, the controller 20 responds by activating a power drive mode that rotates the at least one wheel 30 to propel the patient support apparatus 10.

Referring now to FIG. 1, the patient support apparatus 10 may include a hospital bed. While illustrated as a bed, it is within the scope of the disclosure that the patient support apparatus 10 may include a bed frame, a mattress, or any suitable structure for supporting a patient, including, but not limited to: other types of beds, surgical tables, examination tables, stretchers, and the like.

In some examples, the frame 12 may be in the form of a base frame 12, and an upper frame 24 may be coupled with the base frame 12. The upper frame 24 may be operable between raised, lowered, and tilted positions relative to the base frame 12. The patient support apparatus 10 may include a surface, such as a mattress 26, supported by one of the base frame 12 and the upper frame 24. At least one pair of casters 28 in contact with an underlying floor surface, S, may be coupled to the frame 12. The patient support apparatus 10 further includes at least one wheel 30 coupled to the frame 12, which may include via an axle 31. The at least one wheel 30 may include a pair of wheels 30 or a plurality of wheels 30. The wheels 30 are configured to rotate in a power drive mode in order to propel the patient support apparatus 10 for transportation by a caregiver, or user 22. The patient support apparatus 10 may include a head end 32 and a foot end 34. A head-end base 33 may be provided at the head end 32. A footboard 36 may be provided at the foot end 34 and a headboard 40 may be provided at the head end 32. The patient support apparatus 10 may include a pair of head siderail assemblies 44 and a pair of foot siderail assemblies 48. In some examples, a graphical user interface 52 may be coupled to an external side of at least one siderail of the head and foot siderail assemblies 44, 48.

As illustrated in FIG. 1, the patient support apparatus 10 includes a vertical transport structure in the form of a pair of, or two, transport handles 14. However, it is within the scope of the disclosure for the vertical transport structure to include any structure of the patient support apparatus 10 that aids in propulsion of the patient support apparatus 10. For example, a generally upright shaft forming at least a portion of an intravenous (IV) pole, a support arm or a traction system may be configured according to various aspects described herein. In another example, the vertical transport structure is coupled to, or extends from, the head-end base 33. However, the vertical transport structure is not limited to such examples. The transport handles 14 may be in the form of a metal tube, or a shaft, but are not limited to such constructions and materials. As illustrated, a bottom portion 14a of the transport handles 14 is coupled with the head end 32 such that the transport handles 14 extend substantially perpendicular, orthogonal, or plumb, from the floor surface, S. However, the transport handles 14 may be additionally, or alternatively, coupled with the foot end 34. It is within the scope of the disclosure for the patient support apparatus 10 to include only one, two, or more transport handles 14, including as many as four transport handles 14.

A bellows 56 may be disposed at the bottom portion 14a of the transport handles 14 to cover a mechanical, rotational, joint configured to fold, or collapse, the transport handles 14 from an upward position, which may be generally vertical, to a downward position, which may be generally horizontal. For example, the transport handles 14 may fold, or rotate, at a 90° angle. However, the transport handles 14 may fold to any position in between vertical and horizontal. In this way, the transport handles 14 may be stowed on the head end 32. The bellows 56 may fluidly seal the mechanical joint such that fluids cannot come into contact with the mechanical joint.

Figure 2:
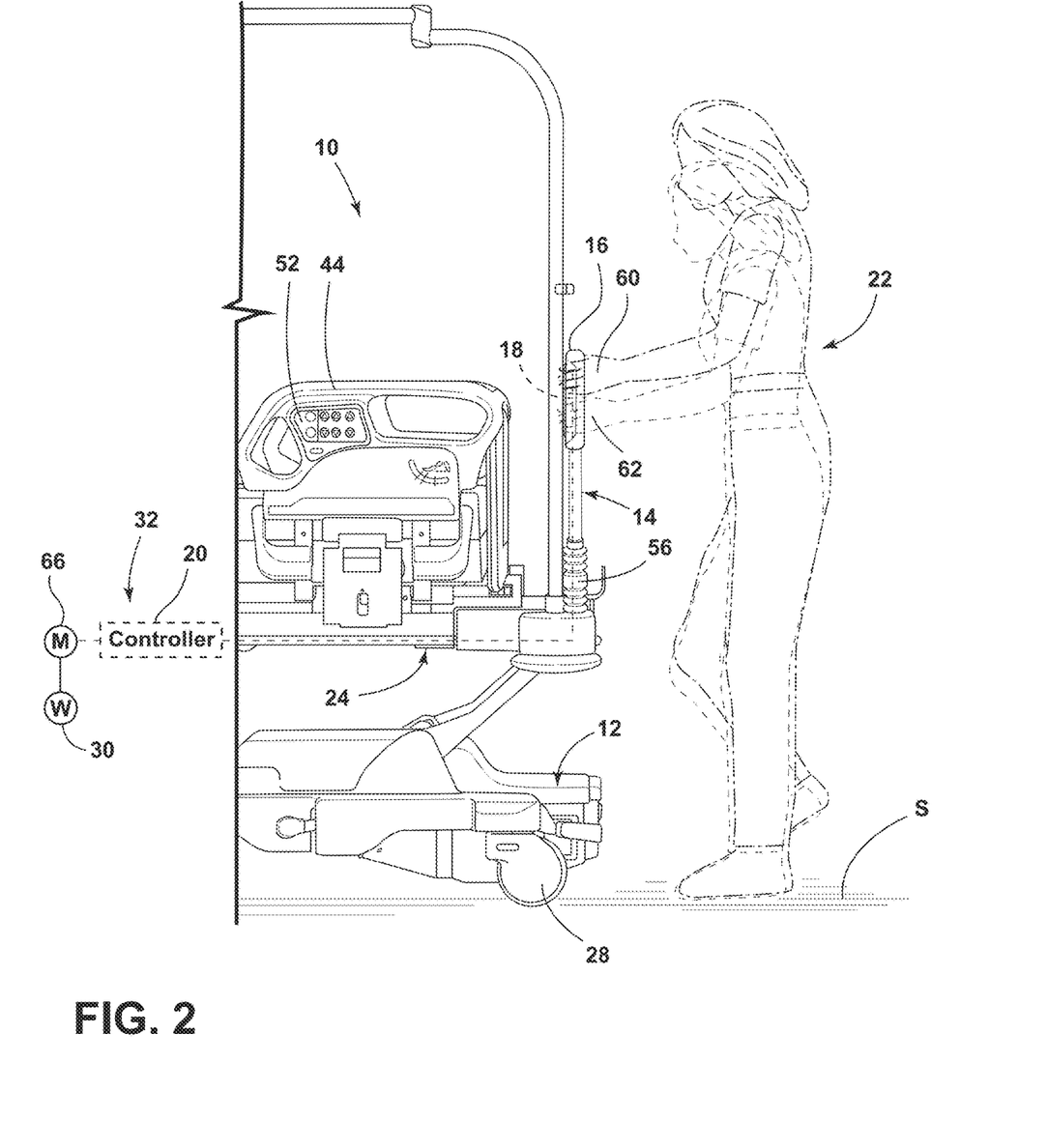
FIG. 2 is a partial side elevational view of a transport handle, according to various aspects described herein.

With reference to FIG. 2, the user 22 is illustrated gripping, or pushing, the transport handle 14 in an upper position 60 and a lower position 62 on the grip 16. As the grip 16 may be in a fixed position relative to the transport handle 14 and/or the base frame 12, the grip 16 may accommodate different user heights. In this way, the user 22 may grip the grip 16 at a comfortable position without raising or lowering the transport handle 14 or the upper frame 24. The grip 16 may be made of a polymeric, rubber-like material, which may include a thermoplastic elastomer (TPE). In some examples, the grip 16 is made of a thermoplastic vulcanizate (TPV), such as Santoprene™. The grip sensor 18 may be provided in the grip 16 and may be in communication with the controller 20.

The controller 20 may be in communication with the patient support apparatus 10 and/or the transport handle 14 for gathering input, processing the input, and generating an output in response to the input. In some examples, the controller 20 is in the form of a microcontroller and may include one or more central processing units (CPUs), or microprocessors, memory, and programmable input/output ports. The input may be provided to the controller 20 from various sensors, including the grip sensor 18, in electrical communication with the transport handle 14, which may be output to the controller 20. The controller 20 may analyze the input in order to command the operation of functions of the patient support apparatus 10, such as the power drive mode, based on the input. For example, a power drive system may include an electric motor 66 coupled with the axle 31 (FIG. 1), which may couple the motor 66 to the pair of wheels 30. The controller 20 may control the operation of the motor 66 in order to initiate the power drive mode by rotating the wheels 30 in response to input, such as an electrical signal, from at least one of the transport handles 14, which may include pushing, pulling, or grabbing of the grip 16 by the user 22. As such, the user 22 can provide input to the controller 20 via a user applied force applied the grip 16. If the controller 20 determines that all the conditions to activate the power drive mode are met, the controller 20 applies power to the motor 66 to propel the wheels 30 of patient support apparatus 10 in one of a forward (i.e., the foot end 34 is leading the way) or reverse direction (i.e., the head end 32 is leading the way).

It may be beneficial for the user 22 to push the transport handles 14 such that the user's forearms may be generally parallel with the floor, which may include a position slightly below an elbow of the user 22. An example of which is described in Zhou, J., & Wiggermann, N. (2017). Ergonomic evaluation of brake pedal and push handle locations on hospital beds. *Applied Ergonomics,* 60, 305-312. Therefore, users 22 of different heights may benefit from positioning their hands on different locations of the transport handles 14 in order to form a more ergonomic posture for pushing the patient support apparatus 10. As such, the grips 16 may be positioned on the transport handles 14 and may be configured to accommodate more than one hand position or grip point. The grip 16 may have a length of approximately 15 to 35 centimeters (approximately 5.906 to 13.78 inches) to provide for the upper position 60 and the lower position 62. In some examples, the preferred grip 16 length may be approximately 30 centimeters (approximately 11.81 inches). It is possible that the grip 16 includes more than two hand positions, which will be discussed with reference to FIGS. 3A-3C. The length of the transport handles 14 may vary depending on where the transport handles 14 are coupled to the patient support apparatus 10. Accordingly, the transport handles 14 may be long enough to position the grips 16 along the length of the transport handles 14 at vertical positons, or heights, in the range of approximately 90 to 115 centimeters from the floor surface, S. In some aspects, the grips 16 are laterally spaced such that the user 22 can simultaneously position left and right hands on a corresponding left and right grip 16. Further, the grips 16 may include approximately equal vertical positions from the floor surface, S, or the head end 32.

Figure 3A:
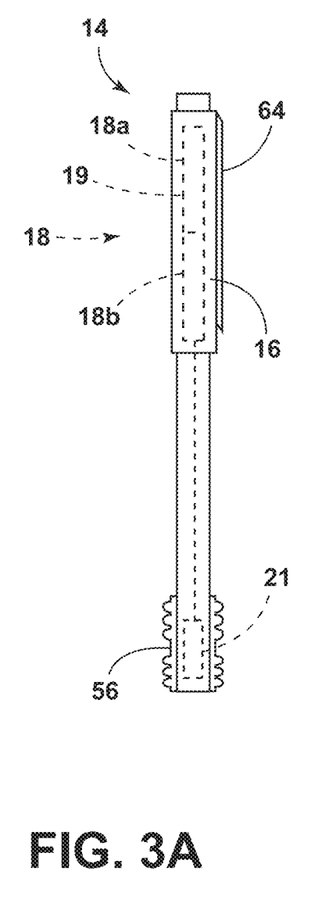
FIG. 3A is a schematic view of the transport handle of FIG. 2 according to various aspects described herein.

Referring now to FIG. 3A, a schematic view of the transport handle 14 is illustrated, according to various aspects described herein. The grip sensor 18 may have a length approximately equal to the length of the grip 16 such that the grip sensor 18 spans almost the entire grip 16. Thus, the user may apply force to the grip sensor 18 by pushing or pulling the grip 16 at any location in order to activate the power drive mode. The grip sensor 18 may be in the form of at least one fail-safe switch 19. In some examples, a plurality of fail-safe switches 19 may be wired in parallel such that the user 22 can grip the transport handle 14 in multiple locations to activate the power drive mode. For example, the grip 16 may include an upper switch 18a and a lower switch 18b wired in parallel to the upper switch 18a. Therefore, upon triggering either of the upper switch 18a or the lower switch 18b, a circuit coupling the upper switch 18a and the lower switch 18b may close and allow electric current to flow and generate a signal. The signal may be output to the controller 20 such that the controller 20 has knowledge of which switch 18a or 18b was activated by the user 22. Accordingly, the controller 20 can determine a vertical position of the user applied force for activating the power drive mode. While described as having the upper switch 18a and the lower switch 18b, it is contemplated that the grip sensor 18 may include more than two switches, which may include the upper switch 18a, the lower switch 18b, and a middle switch. In some aspects, a greater amount of user applied force to the upper switch 18a is required to activate the power drive mode than an amount of user applied force to the lower switch 18b required to activate the power drive mode. Furthermore, the grip sensor 18 may be any sensor suitable for detecting or measuring a user applied torque or force value, including but not limited to: a capacitance sensor, a piezoelectric sensor, a strain sensor, a load cell, and the like. An enable button 64 may be provided to facilitate the triggering of the grip sensor 18 and/or the upper and lower switches 18a and 18b when a force is applied to the button 64.

The grip sensor 18 may include a strain gauge assembly 21 having a load cell, which may be provided in or near the head-end base 33 and may be in electrical communication with the fail-safe switch 19. In some examples, the strain gauge assembly 21 is disposed within the bellows 56. However, the grip sensor 18 may include the strain gauge assembly 21 without a fail-safe switch 19. The load cell may include four strain gauges or resistors, which are electrically coupled to form a Wheatstone bridge. The Wheatstone bridge is used to find an unknown resistance, which may include user 22 applied force on the transport handle 14 and/or grip 16, deflection of the transport handle 14, or other position or force related characteristics. In some examples, detection of forward/reverse deflection of the transport handle detected by the strain gauge assembly 21 or another sensor can be input to the controller 20 for activating forward or reverse power drive modes. Optionally, the transport handle 14 may further include a forward/reverse toggle, or rocker switch. The forward/reverse toggle switch is moved to a forward position in which the electric motor 66 operates to drive the pair of wheels 30 in a forward direction to propel the patient support apparatus 10 in the forward direction, and the forward/reverse toggle switch is moved to a reverse position in which the electric motor 66 operates to drive the pair of wheels 30 in a reverse direction to propel the patient support apparatus 10 in the reverse direction.

Figure 3B:
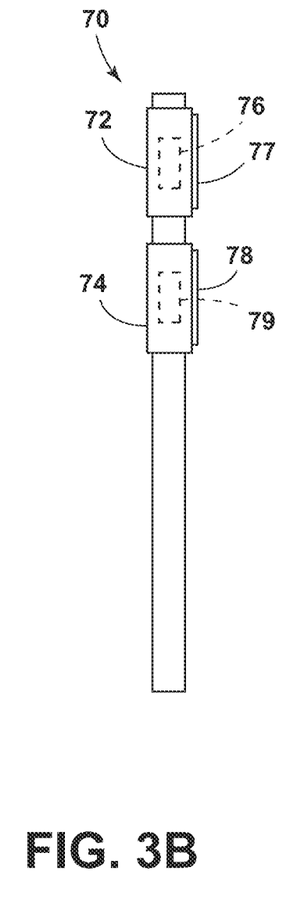
FIG. 3B is a schematic view of a transport handle, according to various aspects described herein.

FIG. 3B illustrates a schematic view of a transport handle 70, according to various aspects described herein. The transport handle 70 may include an upper grip 72 and a lower grip 74. An upper grip sensor 76 and a lower grip sensor 78 may be provided in the upper grip 72 and a lower grip 74, respectively. The transport handle 70 may further include an upper enable button 77 and a lower enable button 79. Similar to the grip sensor 18, the upper grip sensor 76 and the lower grip sensor 78 may be any sensor suitable for detecting or measuring torque or force values. In some examples, the controller 20 may activate the power drive mode upon measuring or detecting a push force threshold value, or a minimum value. In this way, the power drive mode may activate consistently when a particular force is applied to the transport handle 70. The push force threshold value may correspond to the determined vertical position of the user applied force. The threshold value may be approximately three pound-force (approximately 13.34 N). Additionally, it is within the scope of aspects described herein for a speed of the patient support apparatus 10 in the power drive mode to increase with an increasing push force by the user 22. The push force may be calculated with the equation:

Force=Torque/Distance

Thus, the distance, or location, of the grip point may be determined to more accurately measure the push force applied to the transport handle 70 by the user 22.

The upper grip sensor 76 and the lower grip sensor 78 may be wired separately.

In this way, the controller 20 detects which of the upper or lower grip sensors 76, 78 is activated. As the controller 20 may have knowledge of the height, or location, of the upper and lower grip sensors 76, 78, the force applied to the transport handle 70 may be calculated from the measured torque value. As the upper grip sensor 76 may have more distance (i.e. it is located in a higher position on the transport handle 70) than the lower grip sensor 78, the upper grip sensor 76 may require a greater amount of torque to reach the push force threshold value and to activate the power drive mode. Therefore, the lower grip sensor 78 may require a lesser amount of torque to reach the push force threshold value than the amount of torque necessary for the upper grip sensor 76.

Figure 3C:
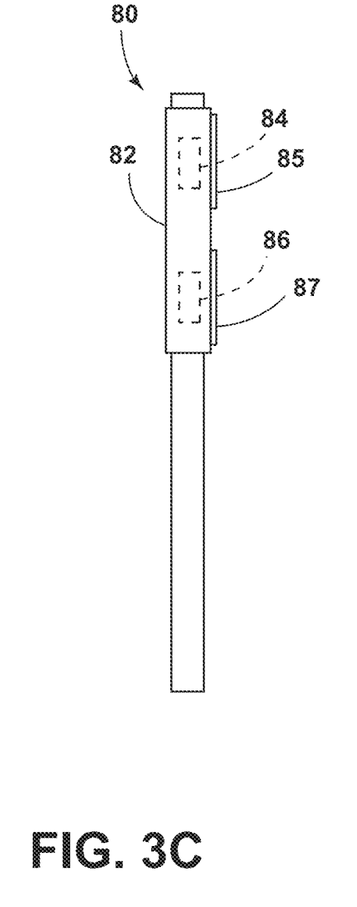
FIG. 3C is a schematic view of a transport handle, according to various aspects described herein.

FIG. 3C illustrates a schematic view of a transport handle 80, according to various aspects described herein. The transport handle 80 is similar to the transport handle 70. Therefore, the description with respect to the transport handle 70 applies to the transport handle 80, and the description with respect to the transport handle 80 applies to the transport handle 70. Alternatively to an upper grip and a lower grip, the transport handle 80 may include a single, continuous grip 82. An upper grip sensor 84 and a lower grip sensor 86 may be provided in the single, continuous grip 82. The transport handle 80 may further include an upper enable button 85 and a lower enable button 87.

The upper grip sensor 84 and the lower grip sensor 86 may be wired separately. In this way, the controller 20 may detect which of the upper or lower grip sensors 84, 86 is activated. Additionally, the controller 20 may detect that both of the upper and lower grip sensors 84, 86 are activated. Again, the upper grip sensor 84 may require a greater amount of torque to reach the push force threshold value and to activate the power drive mode than the lower grip sensor 86. In the case where both of the upper grip sensor 84 and the lower grip sensor 86 are activated, the controller 20 may determine the push force threshold value with an amount of torque greater than the amount of torque required for activation of the power drive mode with only the lower grip sensor 86, and less than the amount of torque required with only the upper grip sensor 84. Stated another way, a medium amount of torque may be required to activate the power drive mode when both of the upper grip sensor 84 and the lower grip sensor 86 are activated. Therefore, the controller 20 may determine consistent push force values for users of varying heights. While illustrated as straight, vertical handles, 14, 70, and 80, it is within the scope of aspects described herein for at least a portion of the handles 14, 70, and 80 to have a curved, or angled, construction.

Figure 4:
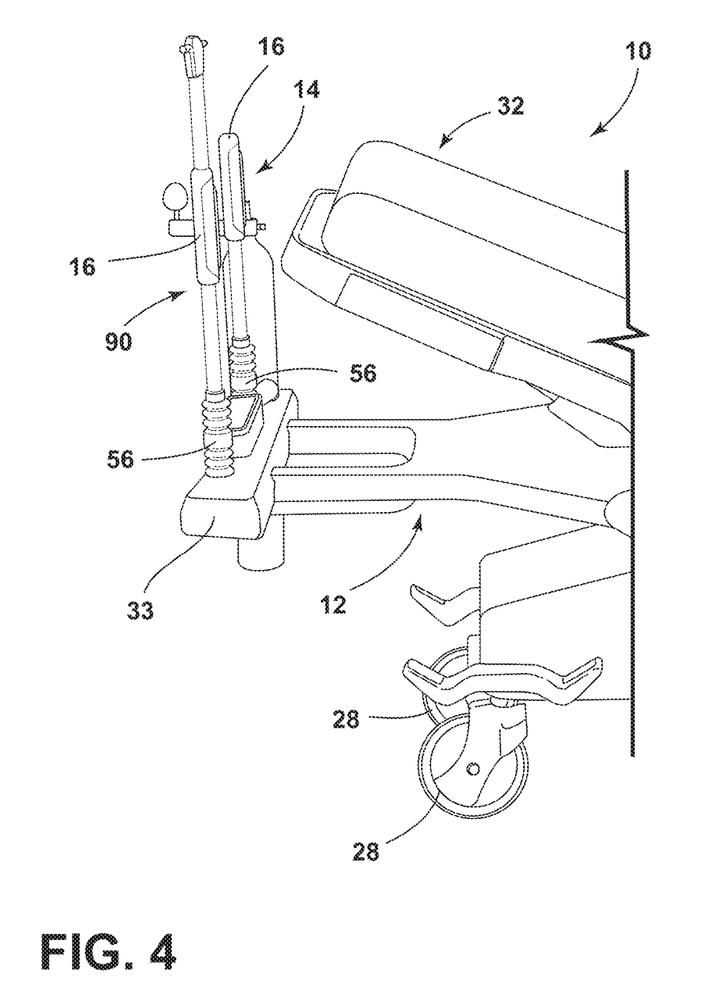
FIG. 4 is a partial side elevational view of transport handles, according to various aspects described herein.

Referring now to FIG. 4, a transport handle 90 and the transport handle 14 are illustrated, according to various aspects described herein. The transport handle 90 may include the grip 16. However, the transport handle 90 may instead include any other suitable grip known in the art. Moreover, any of the grips, such as grips 72, 74 and 82, described herein may be configured with either of the transport handles 14 and 90. While FIG. 4 illustrates the patient support apparatus 10 including one transport handle 90 and one transport handle 14, it is within the scope of the disclosure for the patient support apparatus 10 to include more than one transport handle 90. The transport handle 90 may be configured as an intravenous (IV) pole. In this way, it may not be necessary for the patient support apparatus 10 to include a separate IV pole, thereby allowing for the reduction of clutter around the head end 32 or foot end 34 of the patient support apparatus 10. Additionally, the transport handle 90 may include a strain gauge assembly having a load cell.

Figure 5:
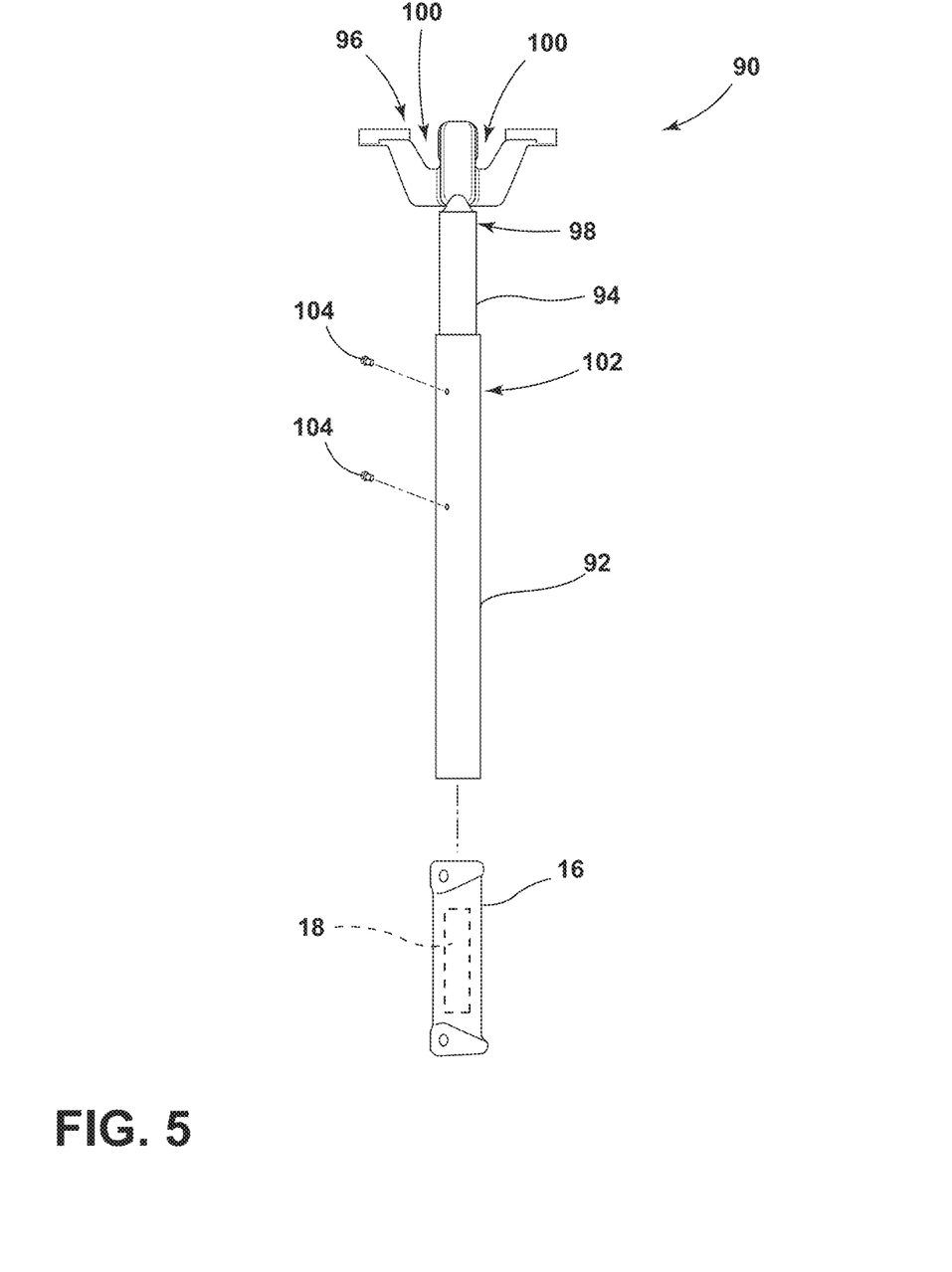
FIG. 5 is a side elevational exploded view of the transport handle of FIG. 2, according to various aspects described herein.

FIG. 5 is an exploded view of the transport handle 90, according to various aspects described herein. The transport handle 90 may be configured as a vertical transport handle 90 including an outer shaft 92 and an inner shaft 94. The outer and inner shafts 92, 94 may be in the form of poles, which may be hollow and made from any suitable material, such as a metal or plastic. The inner shaft 94 may be slidable within the outer shaft 92 such that the transport handle 90 includes a telescoping configuration for height adjustment. The inner shaft 94 may include a hook assembly 96 at an upper end 98. The hook assembly 96 may be generally "W" shaped such that two hooking portions 100 are provided. However, the hook assembly 96 may be any suitable configuration for securing an object, such as a flexible fluid container.

The grip 16 may be positioned at an upper end 102 of the outer shaft 92. In some examples, in order to assemble the grip 16 on the transport handle 90, the grip may be slid over the outer shaft 92 into position and secured with fasteners 104. The fasteners 104 may be a length which does not interfere with the telescoping functionality of the inner shaft 94 within the outer shaft 92. A variety of height adjusting mechanisms may be incorporated into the transport handle 90 for adjusting the height of the inner shaft 94 relative to the outer shaft 92. In some examples, the height adjusting mechanism includes a single-sided or dual-sided push button spring. In another example, an inside surface of the outer shaft 92 includes threads, which may be rotatably coupled with threads on an outside surface of the inner shaft 94. Thus, the inner shaft 94 may travel up and down relative to the outer shaft 92 by rotation of the inner shaft 94. A locking mechanism may be provided to prevent undesirable movement of the inner shaft 94.

Figure 6:
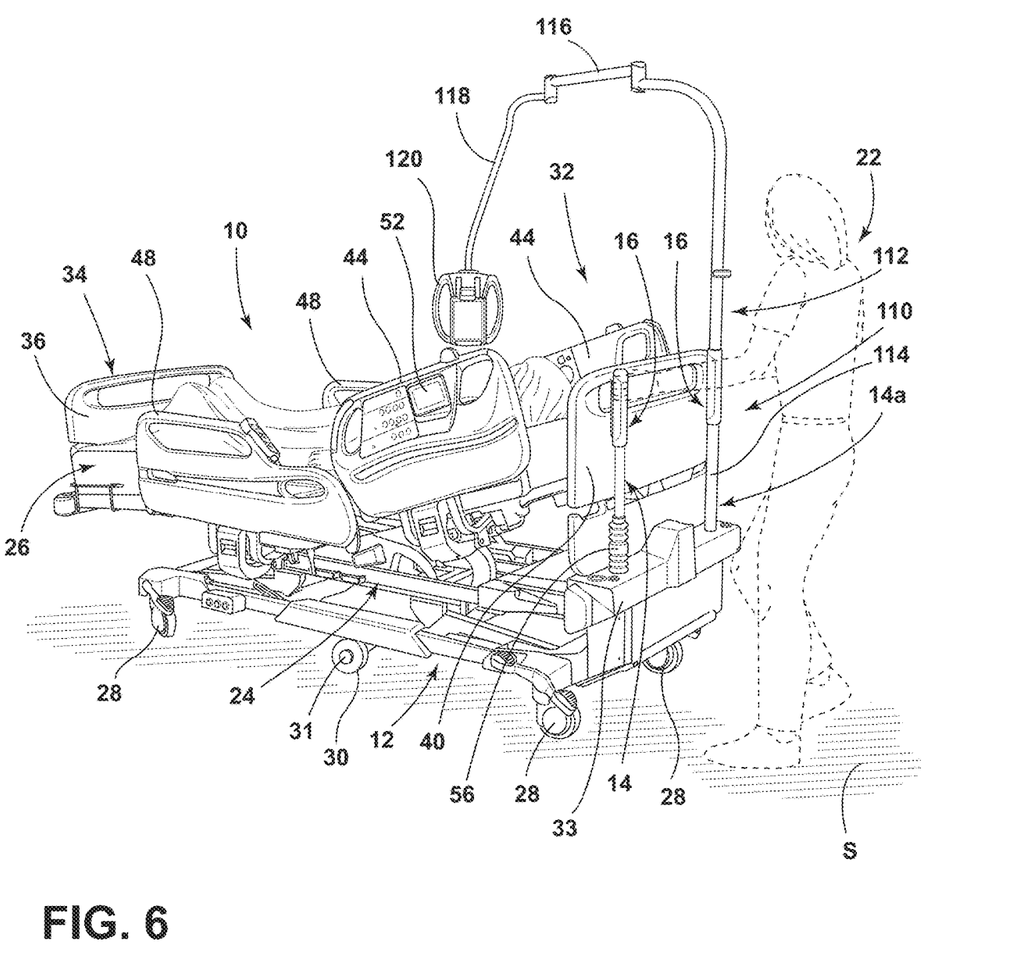
FIG. 6 is a top perspective view of a transport structure, according to various aspects described herein.

Referring now to FIG. 6, a transport structure 110 and the transport handle 14 are illustrated, according to various aspects described herein. The transport structure 110 may include the grip 16. The illustrative transport structure 110 is in the form of a support arm 112 coupled with the head-end base 33 at the head end 32 of the patient support apparatus 10. The support arm 112 may include a fixed portion 114 in the form of an upright shaft and a pivotable portion 116. The pivotable portion 116 may extend laterally from the fixed portion 114 and may be configured to rotate relative to the fixed portion 114. A strand, or cord 118, may depend from the pivotable portion 116 and may be repositioned to a variety of locations about the patient support apparatus 10. A user interface housing 120 may be coupled with the cord 118. As illustrated, the fixed portion 114 includes the grip 16.

While FIG. 6 illustrates the patient support apparatus 10 including one transport structure 110 and one transport handle 14, it is within the scope of the disclosure for the patient support apparatus 10 to include any combination of transport structures and/or handles described herein. As the transport structure 110 may be configured as a support arm 112, it may not be necessary for the patient support apparatus 10 to include a pair of transport handles 14, thereby allowing for the reduction of clutter around the head end 32 or foot end 34 while providing the user 22 with the grip 16 to use for propulsion of the patient support apparatus 10.

Figure 7:
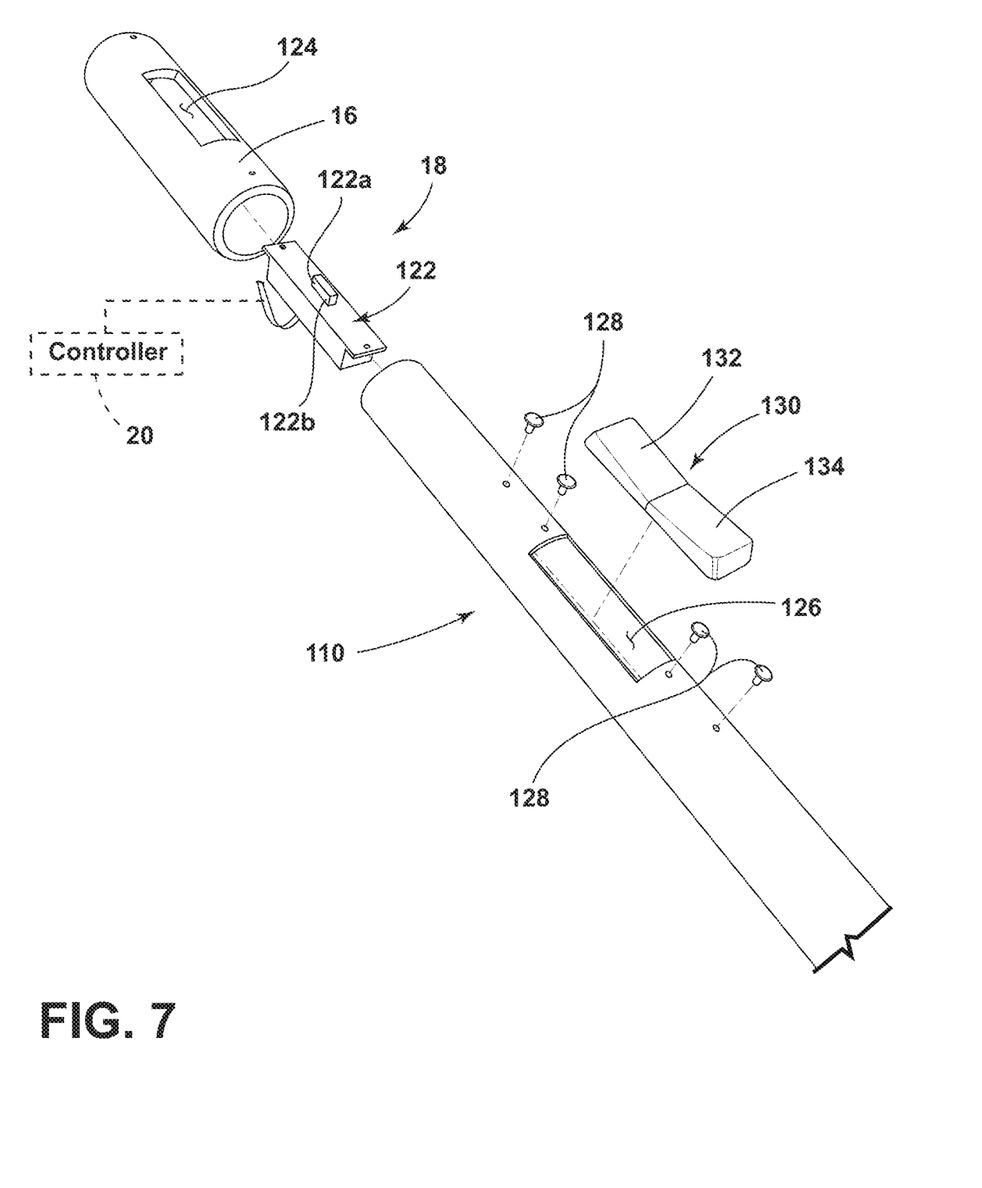
FIG. 7 is a side perspective exploded view of the transport structure of FIG. 6, according to various aspects described herein.

Referring now to FIG. 7, the grip sensor 18 coupled to the grip 16 on the transport structure 110 may be in the form of a rocker switch 122. However, the transport handle 14 and the transport structure 110 may include any of the grips, such as grips 72, 74 and 82 described herein. Further, it is within the scope of this disclosure for other types of buttons or switches to be used, such as fail-safe switches, membrane switches, toggle switches, push button switches, or combinations thereof.

The illustrative rocker switch 122 may include a projection having a first end 122a and a second end 122b in electrical communication with the controller 20. The grip 16 may define an aperture 124 that aligns with an aperture 126 defined by the transport structure 110 when the grip 16 is in a mounted state. The rocker switch 122 may be disposed within the transport structure 110 in alignment with the apertures 124, 126. Fasteners 128 may be provided to mount the rocker switch 122 and the grip 16 to machined portions of the transport structure 110. Further, a rocker switch button 130 may be coupled with the rocker switch 122 and extend from the aperture 124. In this way, the aperture 124 retains the rocker switch button 130. The illustrative rocker switch button 130 includes a forward portion 132 and a reverse portion 134. When the user applies force to the forward portion 132, the rocker switch button 130 depresses the first end 122*a* of the rocker switch 122, which sends an electrical signal to the controller 20 that the controller 20 can interpret as a signal to activate the power drive mode and propel the patient support apparatus 10 in the forward direction. Along these lines, when the user applies force to the reverse portion 134, the rocker switch button 130 depresses the second end 122*b* of the rocker switch 122, which sends an electrical signal to the controller 20 that the controller 20 can interpret as a signal to activate the power drive mode and propel the patient support apparatus 10 in the reverse direction. The rocker switch 122 and the rocker switch button 130 can include any suitable configuration. In some examples, the rocker switch 122 and the rocker switch button 130 include a three-position momentary center-neutral configuration, which have a center position that can perform an OFF or NEUTRAL function where a signal is not sent to the controller 20 to activate the power drive mode.

Figure 8:
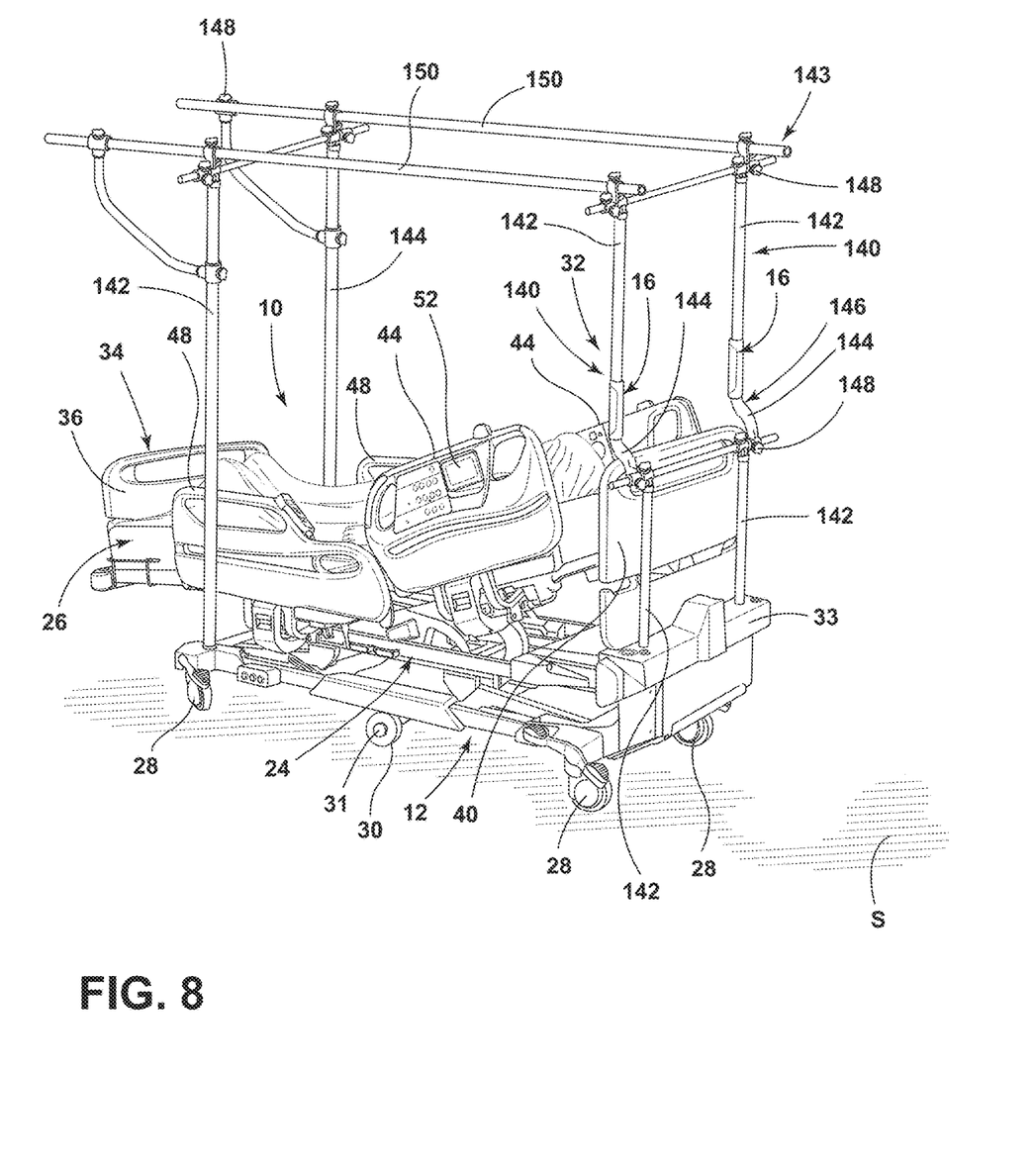
FIG. 8 is a top perspective view of another transport structure, according to various aspects described herein.

Referring now to FIG. 8, transport structures 140 are illustrated, according to various aspects described herein. The illustrative transport structures 140 are in the form of vertical traction components 142 of a traction assembly 143, which are coupled with the head end 32 of the patient support apparatus 10. The traction assembly 143 may include a framework of bars, pulleys, cords and weights. The vertical traction component 142 may include a fixed portion 144 in the form of an upright shaft, or bar. In some examples, the vertical traction components 142 include a bent portion 146. One or more knobs 148 may be provided to adjust the positioning of the vertical traction components 142. The traction assembly 143 may also include horizontal traction components 150 coupled with the vertical traction components 142. As illustrated, the fixed portion 144 includes the grip 16 that aids in propulsion of the patient support apparatus 10. Moreover, any of the grips, such as grips 72, 74 and 82, described herein may be configured with the transport structures 140.

While FIG. 8 illustrates the patient support apparatus 10 including a pair of the transport structures 140, it is within the scope of the disclosure for the patient support apparatus 10 to include any combination of transport structures and/or handles described herein, which may include a single transport structure 140 and a handle 14. As the transport structure 140 may be configured as a vertical traction component 142, it may not be necessary for the patient support apparatus 10 to include a pair of transport handles 14, thereby allowing for the reduction of clutter around the head end 32 or foot end 34 while providing the user 22 with the grip 16 to use for propulsion of the patient support apparatus 10.

Figure 9:
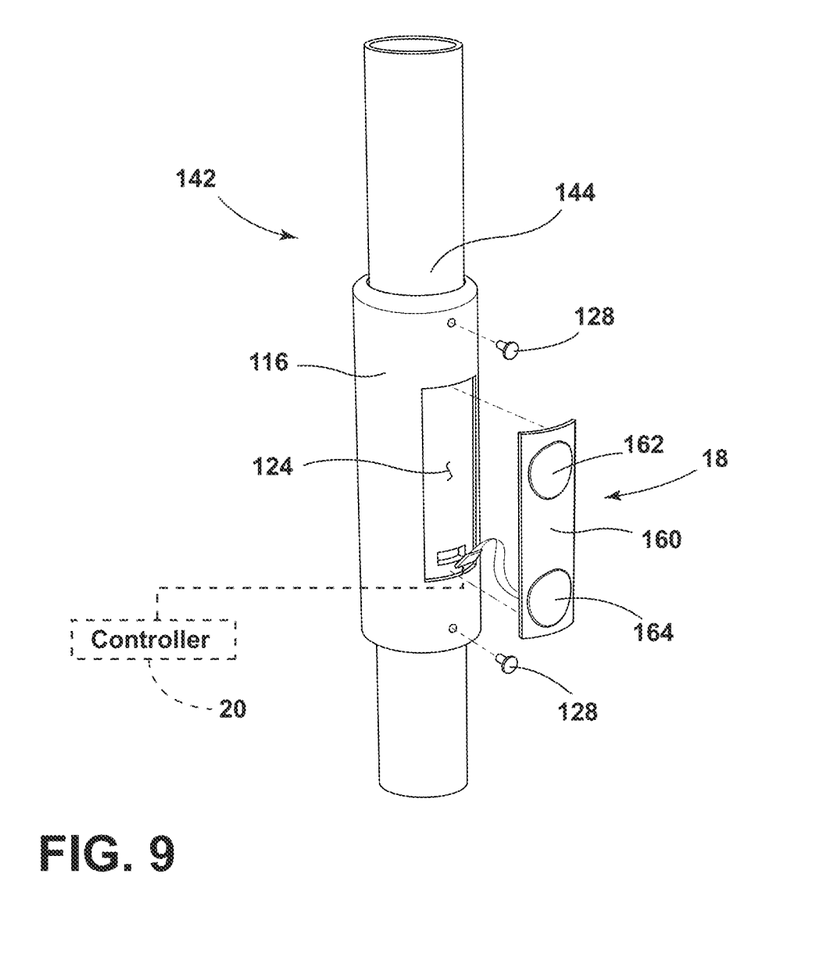
FIG. 9 is a top perspective exploded view of the transport structure of FIG. 8, according to various aspects described herein.

FIG. 9 illustrates the fixed portion 144 of the vertical traction component 142 including the grip sensor 18 coupled to the grip 16 in the form of a membrane switch 160. However, the vertical traction component 142 may include any of the grips, such as grips 72, 74 and 82 described herein. Further, it is within the scope of this disclosure for other types of buttons or switches to be used, such as fail-safe switches, rocker switches, toggle switches, push button switches, or combinations thereof.

The illustrative membrane switch 160 is in electrical communication with the controller 20. The grip 16 may define the aperture 124 for positioning of the membrane switch 160. The membrane switch 160 may include a forward switch 162 and a reverse switch 164. When the user applies force to the forward switch 162 the membrane switch 160 sends an electrical signal to the controller 20 that the controller 20 can interpret as a signal to activate the power drive mode and propel the patient support apparatus 10 in the forward direction. Similarly, when the user applies force to the reverse switch 164, the membrane switch 160 sends an electrical signal to the controller 20 that the controller 20 can interpret as a signal to activate the power drive mode and propel the patient support apparatus 10 in the reverse direction. The membrane switch 160 may include any suitable configuration, which may include a momentary switch device having at least one contact on, or made of, a flexible substrate.

Figure 10:
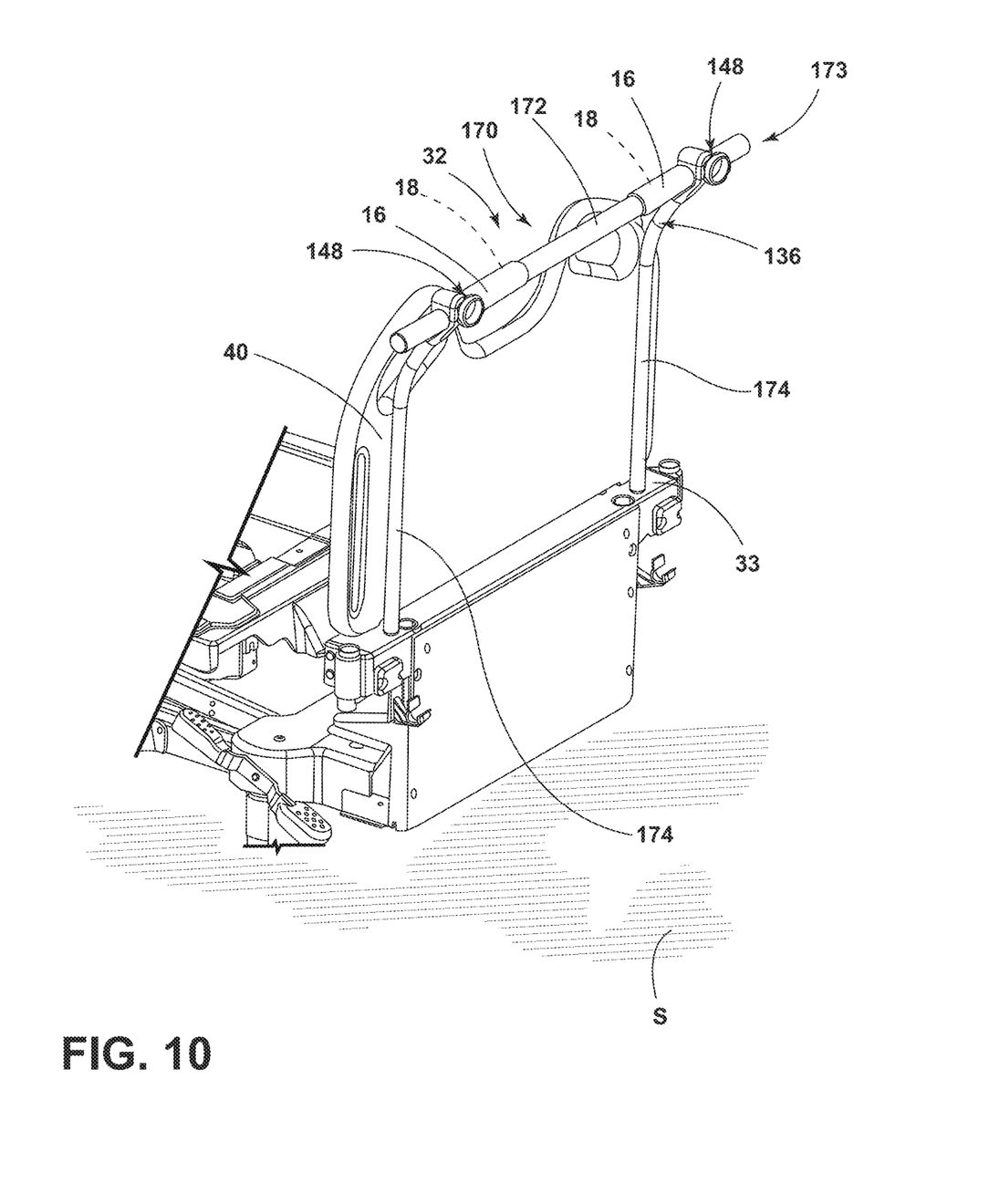
FIG. 10 is a top perspective view of yet another transport structure, according to various aspects described herein.

Referring now to FIG. 10, a transport structure 170 is illustrated, according to various aspects described herein. The illustrative transport structure 170 is in the form of a horizontal traction component 172 of a traction assembly 173, which is coupled with the head end 32 of the patient support apparatus 10 via vertical traction components 174 at the head-end base 33. The horizontal traction component 172 may be in the form of a shaft, or bar that is generally parallel with the floor surface, S.

The horizontal traction component 172 of the transport structure 170 may include a pair of the grips 16 that aid in propulsion of the patient support apparatus 10. Moreover, any of the grips, such as grips 72, 74 and 82, described herein may be configured with the transport structure 170. The grips 16 are spaced apart and may include lengths that accommodate various user heights and shoulder widths. As the transport structure 170 may be configured as a horizontal traction component 172, it may not be necessary for the patient support apparatus 10 to include a pair of transport handles 14, thereby allowing for the reduction of clutter around the head end 32 or foot end 34 while providing the user 22 with the grips 16 to use for propulsion of the patient support apparatus 10. The grip sensor 18 coupled to the grip 16 may be in the form of a rocker switch. However, the transport structure 170 may include any of the grips, such as grips 72, 74 and 82 described herein. Further, it is within the scope of this disclosure for other types of buttons or switches to be used, such as fail-safe switches, membrane switches, toggle switches, push button switches, or combinations thereof.

According to one aspect of the present disclosure, a patient support apparatus may include a frame, a vertical transport handle coupled with the frame and having a grip including at least one grip sensor, and a controller. The controller may be configured to determine a location and a torque applied to the at least one grip sensor for determining a push force when a user pushes the grip. A power drive mode may be activated upon the push force reaching a threshold value.

According to another aspect of the present disclosure, at least one grip sensor further includes an upper grip sensor and a lower grip sensor.

According to still another aspect of the present disclosure, a greater amount of torque is required to activate a power drive mode when an upper grip sensor is pushed than an amount of torque required to activate the power drive mode when a lower grip sensor is pushed.

According to yet another aspect of the present disclosure, an upper grip sensor and a lower grip sensor further includes an upper fail-safe switch and a lower fail-safe switch.

According to still another aspect of the present disclosure, at least one grip sensor further includes a fail-safe switch having a length approximately equal to a length of a grip.

According to still another aspect of the present disclosure, a fail-safe switch further includes an upper switch and a lower switch wired in parallel with the upper switch.

According to yet another aspect of the present disclosure, a threshold value may correspond to a push force required to close a circuit between an upper switch and a lower switch.

According to a second aspect of the present disclosure, a patient support apparatus may include a frame and a vertical transport handle coupled with the frame. The vertical transport handle may include an outer shaft, a grip coupled with the outer shaft, and an inner shaft slidable within the outer shaft. At least one grip sensor may be provided in the grip. A controller may be configured to determine a torque applied to the at least one grip sensor for determining a push force when a user pushes the grip. The inner shaft may include a hook at an upper end thereof configured to secure an object.

According to another aspect of the present disclosure, an object corresponds to a flexible fluid container.

According to still another aspect of the present disclosure, a power drive mode is activated upon the push force reaching a threshold value.

According to yet another aspect of the present disclosure, a controller is configured to determine a location of a torque applied to at least one grip sensor.

According to still another aspect of the present disclosure, at least one grip sensor further includes an upper sensor and a lower sensor.

According to yet another aspect of the present disclosure, a greater amount of torque may be required to activate a power drive mode when an upper sensor is pushed than an amount of torque required to activate the power drive mode when a lower sensor is pushed.

The various illustrative logical blocks, modules, controllers, and circuits described in connection with the embodiments disclosed herein may be implemented or performed with application specific integrated circuits (ASICs), field programmable gate arrays (FPGAs), general purpose processors, digital signal processors (DSPs) or other logic devices, discrete gates or transistor logic, discrete hardware components, or any combination thereof designed to perform the functions described herein. A general purpose processor may be any conventional processor, controller, microcontroller, state machine or the like. A processor may also be implemented as a combination of computing devices, e.g., a combination of a DSP and a microprocessor, a plurality of microprocessors, one or more microprocessors in conjunction with a DSP core, or any other such configuration.

It is also important to note that the construction and arrangement of the elements of the disclosure, as shown in the exemplary embodiments, is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts, or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

It is also to be understood that variations and modifications can be made on the aforementioned structures and methods without departing from the concepts of the present disclosure, and further it is to be understood that such concepts are intended to be covered by the following claims unless these claims by their language expressly state otherwise.

What is claimed is:

1. A patient support apparatus comprising:
a frame;
at least one wheel coupled to the frame;
a vertical transport handle coupled with the frame;
a grip coupled with the vertical transport handle;
at least one grip sensor coupled to the grip along a vertical length on the vertical transport handle; and
a controller configured to:
determine a vertical position of a user applied force to the grip sensor along the vertical length;
determine a value of user applied torque applied to the at least one grip sensor;
determine a push force value using the determined vertical position and the determined torque value; and
wherein in response to the push force value reaching a threshold value, the controller responds by activating a power drive mode that rotates the at least one wheel to propel the patient support apparatus.

2. The patient support apparatus of claim 1, wherein the at least one grip sensor further includes an upper grip sensor and a lower grip sensor.

3. The patient support apparatus of claim 2, wherein a greater amount of user applied torque to the upper grip sensor is required to activate the power drive mode than an amount of user applied torque to the lower grip sensor required to activate the power drive mode.

4. The patient support apparatus of claim 2, wherein the upper grip sensor and the lower grip sensor further include an upper fail-safe switch and a lower fail-safe switch.

5. The patient support apparatus of claim 1, wherein the at least one grip sensor spans substantially along a length of the grip.

6. The patient support apparatus of claim 5, wherein the at least one grip sensor further includes an upper switch and a lower switch wired in parallel with the upper switch.

7. The patient support apparatus of claim 6, wherein the threshold value corresponds to a push force value required to close a circuit between the upper switch and the lower switch.

8. The patient support apparatus of claim 1, further comprising:
a strain gauge assembly electrically coupled to the grip sensor.

9. The patient support apparatus of claim 1, wherein the grip includes a length of approximately 15 to 35 centimeters and extends substantially orthogonal from a floor surface.

10. A patient support apparatus comprising:
a frame;
a vertical transport structure coupled with the frame;
a grip coupled with the vertical transport structure;
at least one grip sensor coupled to the grip on the vertical transport structure along a vertical length; and
a controller that determines a vertical position of a user applied force applied to the at least one grip sensor along the vertical length, wherein the controller activates a power drive mode upon determining that a push force value has reached a threshold value corresponding to the vertical position of the user applied force and propel patient support apparatus, wherein the push force value is calculated with a user applied torque value divided by a location value corresponding to the vertical position.

11. The patient support apparatus of claim 10, wherein the vertical transport structure comprises a support arm including a cord.

12. The patient support apparatus of claim 10, wherein the at least one grip sensor spans substantially along a length of the grip.

13. The patient support apparatus of claim 10, wherein the vertical transport structure comprises a vertical traction component.

14. The patient support apparatus of claim 10, wherein the at least one grip sensor further includes an upper grip sensor and a lower grip sensor.

15. The patient support apparatus of claim 14, wherein a greater amount of user applied force to the upper grip sensor is required to activate the power drive mode than an amount of user applied force to the lower grip sensor required to activate the power drive mode.

* * * * *